United States Patent [19]

Weber et al.

[11] Patent Number: 4,485,684

[45] Date of Patent: Dec. 4, 1984

[54] APPARATUS FOR EXTRACTING AND ANALYSING DUST-LADEN GAS SAMPLES

[75] Inventors: Rudolf Weber, Oelde; Horst Riedel, Vorhelm, both of Fed. Rep. of Germany

[73] Assignee: Krupp Polysius AG, Beckum, Fed. Rep. of Germany

[21] Appl. No.: 435,109

[22] Filed: Oct. 18, 1982

[30] Foreign Application Priority Data

Nov. 10, 1981 [DE] Fed. Rep. of Germany ... 8132855[U]

[51] Int. Cl.³ .............................................. G01N 1/22
[52] U.S. Cl. .............................. 73/863.12; 73/863.11; 73/863.24; 73/863.86
[58] Field of Search .......... 73/863.11, 863.12, 863.24, 73/863.61, 863.82, 863.83, 863.86, 864.81

[56] References Cited

U.S. PATENT DOCUMENTS

| | | | |
|---|---|---|---|
| 3,457,787 | 7/1969 | Maatsch et al. | 73/863.24 X |
| 3,517,557 | 6/1970 | Granger et al | 73/863.12 |
| 3,675,489 | 7/1972 | Garilli et al. | 73/863.12 |
| 3,680,388 | 8/1972 | Critchley et al. | 73/863.11 |
| 3,748,906 | 7/1973 | Manka | 73/863.24 X |
| 3,807,233 | 4/1974 | Crawford | 73/863.11 |
| 3,950,136 | 4/1976 | Bellinga | 73/863.86 X |
| 3,960,500 | 6/1976 | Ross et al. | 73/863.11 X |
| 3,985,624 | 10/1976 | Prevost et al. | 73/863.12 |
| 4,073,619 | 2/1978 | Lawson | 73/863.11 |
| 4,115,229 | 9/1978 | Capone | 73/863.61 X |
| 4,221,058 | 9/1980 | Zagorzycki | 73/863.11 X |
| 4,259,867 | 4/1981 | Foundos et al. | 73/863.12 |
| 4,336,722 | 6/1982 | Schweitzer | 73/863.12 |

FOREIGN PATENT DOCUMENTS

| | | | |
|---|---|---|---|
| 526569 | 6/1931 | Fed. Rep. of Germany ... | 73/863.12 |
| 1045004 | 10/1966 | United Kingdom ............ | 73/863.12 |

Primary Examiner—Gerald Goldberg
Assistant Examiner—Tom Noland
Attorney, Agent, or Firm—Learman & McCulloch

[57] ABSTRACT

Apparatus for extracting and analyzing dust-laden gas samples and in which a gas extraction connection is constructed in the form of a stilling chamber leading to an analyzer via a three-way valve to which is connected a cleansing air connection. A time control device periodically interrupts the flow of gas to the analyzer and directs cleansing air of the extraction connection.

9 Claims, 1 Drawing Figure

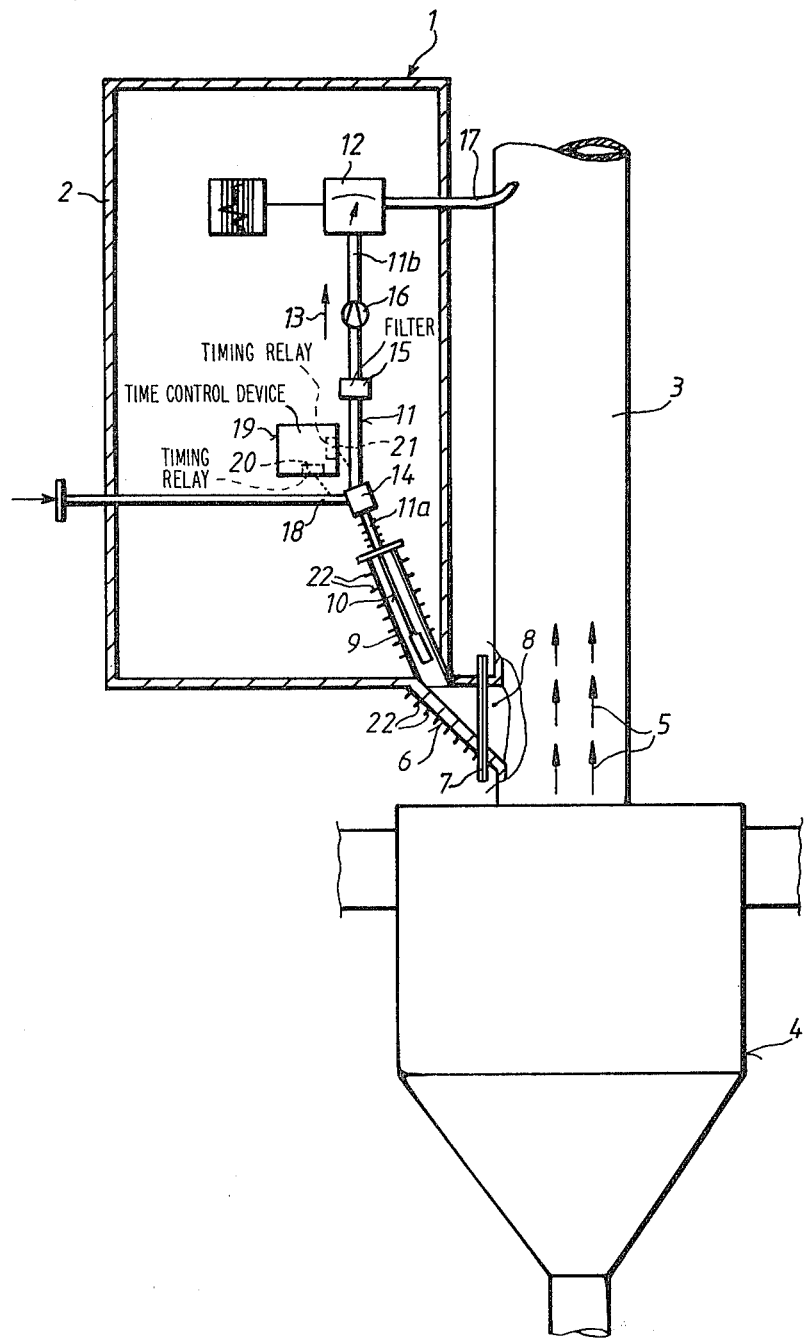

APPARATUS FOR EXTRACTING AND ANALYSING DUST-LADEN GAS SAMPLES

BACKGROUND OF THE INVENTION

The invention relates to apparatus for extracting and analysing dust-laden gas samples, especially for attachment to an exhaust gas line of a heat exchanger in a suspended gas preheater, containing a gas extraction connection, a gas extraction probe associated with the gas extraction connection, an analyzer, a gas sample conveying pipe arranged between the gas extraction probe and the analyzer, and a switch valve in the gas sample conveying pipe.

In known extraction and analysis apparatus which can preferably be built onto an exhaust gas line of a cyclone preheater, one end of the gas sample conveying pipe is constructed in such a way that it can extend into the corresponding exhaust gas line of the preheater and thus forms the gas extraction connection, and a gas extraction probe can also be provided at this point. The gas sample conveying pipe is connected at its other end via an injector to the lower section of the exhaust gas line while being connected by a separate test gas line to the analyzer. The gas sample conveying pipe constantly provides a bypass for a quantity of sampled gas from which a sample can be supplied via the test gas line to the analyzer at predetermined times with at least one switch valve being switched appropriately in the lines.

SUMMARY OF THE INVENTION

An object of the invention is to provide extraction and analysis apparatus of the type described above which is distinguished by its simple construction and by the possibility of relatively simply building it onto a heat exchanger exhaust gas line while at the same time providing the possibility of extracting a gas sample from a quantity of exhaust gas with less turbulent flow.

This object is achieved according to the invention by constructing the gas extraction connection in the form of a stilling chamber, the switch valve being formed by a three-way valve which has a cleansing compressed air connection and is connected to a time control device.

The construction of the apparatus according to the invention with a stilling chamber as the gas extraction connection first of all offers the possibility of extracting the desired gas sample from a quantity of exhaust gas in which the flow has been stilled and from which any heavy dust particles present in the gas can fall out in this stilling chamber, so that breakdowns (especially in the gas extraction probe) caused by large dust particles are to a large extent avoided. With the aid of the time control device the three-way valve can be switched at specific intervals of time so that the cleansing compressed air connection is opened and at the same time the connection to the analyzer is closed, so that compressed air can be blown through the corresponding section of the gas sample conveying pipe, the gas extraction probe and the stilling chamber. The three-way valve can preferably be controlled automatically, so no special operating staff are required for it. These gas extraction and cleansing facilities result in substantially disruption-free operation of the extraction and analysis equipment. Moreover, maintenance work on the said apparatus can be reduced to a minimum and the apparatus requires extremely simple construction.

DESCRIPTION OF THE DRAWING

A preferred embodiment of the invention is described below with the aid of the accompanying drawing FIGURE which is a partly elevational and partly sectional simplified schematic view of the apparatus.

DETAILED DESCRIPTION

The extraction and analysis apparatus 1 according to the invention has a housing 2 which encloses almost all of the parts of the apparatus.

In the preferred embodiment it should be assumed that the apparatus is so constructed that it is built onto an upright exhaust gas line 3 of a known central heat exchanger turbulence shaft, which is part of a suspended gas preheater 4 not shown in greater detail, and through which the exhaust gases (arrow 5) from a rotary kiln or the like (also not shown) flow as is known for example in furnace arrangements for the brick and earth industries or in dressing of ores.

While almost all of the essential parts of the apparatus are accommodated inside the housing 2, a gas extraction connection in the form of a stilling chamber 6 is connected or constructed on the lower end of the housing 2. This stilling chamber 6 is connected for example by flanges 7 to a sample extraction pipe 8 from the exhaust gas line 3. The stilling chamber 6 is preferably shaped and oriented as shown, i.e. it is tapered downwards in the shape of a horizontal half funnel and has the lateral connection already referred to above (by flanges 7) for attachment to the exhaust gas line 3, while on the upper part of the stilling chamber a tubular connecting pipe 9 is provided which preferably extends obliquely upwards into the housing 2.

A gas extraction probe 10 of conventional construction extends approximately coaxially into the connecting pipe 9 from above and the upper part of the probe is connected to the lower section 11a of a gas sample conveying pipe 11, the upper section 11b of which opens into an analyzer 12 of conventional construction. A three-way valve 14 used as a switch valve, a conventional filter 15 with a water separator, and a conventional gas feed pump 16 are arranged one after the other, as viewed in the direction of conveying the gas sample (arrow 13), between the gas extraction probe 10 and the analyzer 12 in the gas sample conveying pipe 11. In the illustrated embodiment an exhaust gas pipe 17 for analyzed gas samples is arranged in the upper part of the apparatus 1, and this exhaust gas pipe 17 communicates between the analyzer 12 and the exhaust gas line 3, projecting a short distance into the latter and opening in the direction of flow of the exhaust gas. Thus, in the present case a bypass line is formed for the gas sample extraction relative to the exhaust gas line 3 of the turbulence shaft 4. However, it should be emphasized at this point that, depending upon the circumstances of the installation of the apparatus 1, the exhaust gas pipe 17 of the analyzer 12 can also be led off in another way.

The three-way valve 14, which preferably is a three-way solenoid valve, has in addition to its two connections to the gas sample conveying pipe 11 a third connection which is formed by a cleansing compressed air connection 18 which can be connected to a compressed air source provided in the usual way in large plants and supplied with compressed air at an appropriately high pressure (for example approximately 6 bars).

The three-way valve 14 is also connected to a time control device 19 which is constructed with two timing relays 20, 21 in such a way that one timing relay 20 effects opening of the cleansing compressed air connection 18 and at the same time the other timing relay 21 briefly closes the upper part of the conveying pipe 11. In this way the essential gas extraction section with the three-way valve 14, the lower section 11a of the conveying pipe, the gas extraction probe 10, and the connecting pipe 9 which are particularly exposed to the dust-laden gas samples can be cleansed with compressed air at specific intervals (for example hourly). This cleansing by compressed air lasts for only a short time, for example only a few seconds, and can be automatically controlled without difficulty. After this cleansing interval the compressed air connection 18 is closed again by the appropriate timing relay 20, while at the same time the other timing relay 21 opens the section of the conveying pipe 11 leading from the three-way valve 14 to the analyzer 12.

The reliability and simplicity of the apparatus 1 can also be advantageously influenced if the gas feed pump 16 is constructed for only a relatively small gas feed capacity of approximately 40–100 l/min, and preferably approximately 60 l/min. In addition it is preferred that this small quantity of sample gas be simultaneously cooled to a convenient temperature, for which purpose, as indicated in the drawing, it is preferable for some or all of the stilling chamber 6, the connecting pipe 9 and the lower section 11a of the conveying pipe to be provided with cooling fins 22.

What is claimed is:

1. In an apparatus for extracting and analyzing samples of dust-laden air from an exhaust gas line of a heat exchanger and including a gas extraction connection in communication with said exhaust gas line, a gas extraction probe, an analyzer, a gas sample pipe communicating with said gas extraction connection for conducting gas samples between said probe and said analyzer, a gas exhaust pipe communicating with said analyzer for exhausting gas remote from said gas extraction connection, and a switch valve in said pipe, the improvement wherein said gas extraction connection comprises a stilling chamber; said switch valve comprises a three-way valve in communication with said gas sample pipe between said probe and said analyzer and with a source of compressed cleansing air; and time control means operable to establish communication between said probe and said air source and simultaneously interrupt communication between said probe and said analyzer, and vice-versa.

2. Apparatus according to claim 1 wherein the stilling chamber is in the shape of a half funnel and has a lateral connection at its large entry end for attachment to said heat exchanger exhaust gas line and a connecting pipe at its small exit end in which the gas extraction probe is accommodated.

3. Apparatus according to claim 1 wherein selected ones of the stilling chamber and the gas sample pipe are provided with cooling means.

4. Apparatus according to claim 3 wherein said cooling means comprises fins.

5. Apparatus according to claim 1 including a gas feed pump in the gas sample pipe.

6. Apparatus according to claim 5 wherein said pump has a capacity of between 40–100 l/min.

7. Apparatus according to claim 5 including a filter with a water separator arranged in the gas sample pipe upstream from said pump.

8. Apparatus according to claim 1 wherein said three-way valve comprises a three-way solenoid valve and said time control means includes two timing relays.

9. Apparatus according to claim 1 wherein said gas exhaust pipe is connected to said heat exchanger exhaust gas line.

* * * * *